United States Patent [19]

Ishida et al.

[11] Patent Number: 4,778,760
[45] Date of Patent: Oct. 18, 1988

[54] THERMOSTABLE α-AMYLASE-PRODUCING, THERMOPHILIC ANAEROBIC BACTERIA, THERMOSTABLE α-AMYLASE AND PROCESS FOR PRODUCING THE SAME

[75] Inventors: Masahiko Ishida; Ryooichi Haga, both of Hitachi; Masako Katsurayama, Katsuta, all of Japan

[73] Assignees: Hitachi, Ltd.; Hitachi Plant Engineering & Construction Co. Ltd., both of Tokyo, Japan

[21] Appl. No.: 795,774

[22] Filed: Nov. 7, 1985

[30] Foreign Application Priority Data

Nov. 9, 1984 [JP] Japan .................. 59-236915
Nov. 9, 1984 [JP] Japan .................. 59-236917

[51] Int. Cl.$^4$ .................. C12N 9/28; C12N 1/20; C12R 1/145
[52] U.S. Cl. .................. 435/202; 435/253; 435/842
[58] Field of Search .................. 435/202, 253, 842

[56] References Cited

U.S. PATENT DOCUMENTS

| | | | |
|---|---|---|---|
| 4,578,352 | 3/1986 | Katkocin et al. | 435/99 |
| 4,600,693 | 7/1986 | Kindle et al. | 435/202 X |
| 4,613,570 | 9/1986 | Zeman | 435/202 |
| 4,642,288 | 2/1987 | Elia De Miguel et al. | 435/99 |

OTHER PUBLICATIONS

Chem. Abstracts, vol. 60, No. 6, Mar. 16, 1964, Column 7173 h, Columbus, Ohio, U.S.; G. J. Walker et al. "Degradation of Starch Granules by Some Amylolytic Bacterial from the Rumen of Sheep" & Biochem. J. 90(2), 398–404 (1964).
Chem. Abstracts, vol. 50, No. 10, May 25, 1956, Col. 7217, h. Columbus, Ohio, U.S.; R. V. Feniksova et al.: "The Preparation of Bacterial Amylase", & Trudy Vsesoyuz. Nauch.–Issledovatel. Inst. Spirtovoi Prom. 1954, No. 3, 128–139; Referat. Zhur. Khim., Biol. Khim. 1955, No. 13338.
Chem. Abstracts, vol. 39, No. 20, Oct. 20, 1945, col. 5261/9, Columbus, Ohio, U.S.; H. Blaschko: "Cysteic Acid Decarboxylase", & Biochem. J. 39, 76–78 (1945).
Chem. Abstracts, vol. 30, No. 4, Feb. 20, 1936, col. 1077/9–col. 1078/1, Columbus, Ohio, U.S.; W. W. Hohnston et al.: "The Amylase of *Clostridium acetobutylicum*" & J. Bact. 30, 491–501 (1935).
Chem. Abstracts, vol. 60, No. 13, Jun. 22, 1964, col. 16234 e, Columbus, Ohio, U.S.; Mikio Tomoeda et al.: "Alpha–Amylase in *Clostridium acetobutylicum*", & Gifu Daigaku Nogakubu Kenkyu.

Primary Examiner—Thomas G. Wiseman
Assistant Examiner—Jayme A. Huleatt
Attorney, Agent, or Firm—Antonelli, Terry & Wands

[57] ABSTRACT

The bacterium producing thermostable α-amylases of this invention is an anaerobic bacterium belonging to Clostridium. The thermostable α-amylases of this invention is novel α-amylases which are excellent in thermostability and acid resistance and have a slight calcium requirement. Said α-amylases are obtained by culturing the aforesaid bacteria and collecting the α-amylases from the culture. When the aforesaid α-amylase is used, sugar production process can be greatly rationalized.

6 Claims, 5 Drawing Sheets

THERMOSTABLE α-AMYLASE-PRODUCING, THERMOPHILIC ANAEROBIC BACTERIA, THERMOSTABLE α-AMYLASE AND PROCESS FOR PRODUCING THE SAME

BACKGROUND OF THE INVENTION

1. Field of the Invention

The first aspect of the present invention relates to anaerobic bacteria used for producing a novel α-amylase, particularly thermostable α-amylase-producing thermophilic anaerobic bacteria suitable for liquefaction reaction of starch in processing starch into glucose etc. and in desizing fiber.

The second aspect of the present invention relates to novel α-amylase and a process for producing the same, particularly to a thermostable α-amylase suitable for liquefaction reaction of starch in starch processing, desizing etc. and a process for producing the same.

2. Description of the Prior Art

Enzymes have a high substrate selectivity and are characterized in that they can catalyze reactions even under ordinary temperature and atmospheric pressure, but in general, they are very unstable to heating and pH change. Recently, it has become possible to produce an isomerized syrup or an L-amino acid by immobilizing an enzyme. In operating such a reactor, it is desired to operate it in a temperature range of 60° C. or above which is higher than ordinary temperature, for preventing the propagation of various undesirable bacteria and/or fungi and for increasing the reaction rate. Therefore, in place of conventional ordinary-temperature enzymes, so-called thermostable enzymes stable to both heating and pH change have heretofore been developed. Conventional thermostable enzymes are produced from aerobic bacteria sources. α-Amylases have heretofore been produced mainly by culturing bacteria belonging to Bacillus which are typical aerobic bacteria (Campbell et al., J. Biol Chem., 236, 2952 (1961)). Among then, α-amylases derived from Bacillus subtilis and Bacillus licheniformis are already industrially produced and are used for processing starch into isomerized syrup, glucose or the like and for desizing fiber. None of these well-known α-amylases of which identity is a protein per se can exhibit their thermostabilities, but they may exhibit the thermostabilities only in the presence of calcium ions. They require a calcium concentration of at least 1 mM (Saito: Japanese Patent Application Kokai (Laid-Open) No. 35,083/73), and the reaction is usually carried out by adding several millimoles to 20 millimoles of a calcium salt (Hattori: Japanese Patent Application Kokai (Laid-Open) Nos. 44,652/76 and 44,690/76). Accordingly, the thermostability of the conventional thermostable α-amylases, for example, α-amylases derived from Bacillus licheniformis extraordinarily decreases in the absence of calcium or the presence of 1 mM or less, if any (see Japanese Patent Application Kokai (Laid-Open) Nos. 12,946/71 and 35,083/73). Therefore, at a very low calcium concentration of 100 μM or less which is equal to the calcium concentration of tap water, α-amylase inactivates during liquefaction reaction of starch, so that a large amount of expensive enzymes are consumed. Accordingly, the reaction is usually carried out by adding several millimoles of a soluble calcium salt such as calcium chloride, calcium acetate or the like. However, when a calcium salt is added, removal of calcium in a subsequent step becomes necessary in producing isomerized syrup or glucose which are product of starch processing.

In general, the optimum pH of α-amylases is 6 or higher, and there are known a very few α-amylases which have a high activity even in acidic pH ranges. For example, as an acid α-amylase, α-amylase of Bacillus licheniformis is known (Tanaka et al.: Japanese Patent Application Kokai (Laid-Open) No. 151,970/77, and Saito: Japanese Patent Application Kokai (Laid-Open) No. 358,083/73). In liquefying a starch, there is used a so-called starch slurry prepared by suspending the starch in a concentration of 10 to 40%, usually 30%, and it has a pH of 5 or lower, frequently 4 or lower because of impurities, organic acids contained in the starting starch. Therefore, as in Ueno: Japanese Patent Application Kokai (Laid-Open) No. 19,049/74 and Nakajima: Japanese Patent Application Kokai (Laid-Open) No. 55,857/74, the starch slurry is always neutralized with calcium hydroxide or calcium carbonate so as to adjust the pH to 6 to 7 and then treated with α-amylase.

The present inventors searched an enzyme and a microorganism for production of the enzyme in order to obtain an α-amylase which is excellent in thermostability, has a high activity even in acidic pH ranges, and has a slight calcium requirement. As a result, the present inventors have found that a strictly anaerobic bacterium belonging to Clostridium (a clostridial bacterium RS-0001, clostridium sp RS-0001, FERM No. 7,918) produces novel α-amylase which is different from conventional α-amylases in enzymatic characteristics, in particular, calcium requirement and pH range for action.

SUMMARY OF THE INVENTION

The first object of this invention is to provide a novel α-amylase-producing microorganism which is excellent in thermostability, has a very slight calcium requirement in thermoresistance, and has a high activity even in acidic pH ranges.

The second object of this invention is to provide a novel α-amylase which is derived from an obligate anaerobic bacterium, is excellent in thermostability, and has a very slight calcium requirement, and a process for producing the same.

The Clostridium sp of this invention is separated from a high-temperature methane fermentation slurry of concentrated organic waste fluid as a source.

The present bacterium was separated in the following manner: First, the methane fermentation slurry was subjected to low-speed centrifugation (1,000 r.p.m., 5 minutes) to precipitate and remove coarse granules, after which the supernatant was diluted with sterilized physiological saline. The diluted supernatant was used as a cell suspension and coated on an agar plate containing starch granules as a carbon source under a nitrogen gas atmosphere, after which the starch granules were anaerobically dissolved at 60° C. and colonies which grew were separated. Further, vegetative cells were isolated from a dilution of the aforesaid colonies by means of a micromanipulator. The separation using an agar plate and the separation by means of a micromanipulator were repeated several times to obtain the bacterium of this invention. The clostridium (Clostridium sp RS-0001) of this invention was deposited in Institute of Microorganism Industrial Science and Technology, Agency of Industrial Science and Technology (Receipt number: Bikoken Kinki No. 7,918 (FERM P-7918)).

Details of micological properties of the present bacterium are explained below:

A. Morphological Properties (1) Shape of vegetative cell

When said bacterium is cultured on an agar plate of the following starch-peptone medium in an anaerobic atmosphere at 60° C. for 2 days, the vegetative cells are a straight bacillus having a size of 0.4–0.8×2–5 μm. When said bacterium is cultured for 3 days or more, vegetative cells having the aforesaid shape exist individually and linked vegetative cells are also produced. The same phenomenon as described above is also observed in the case of submerged culture. The composition of the starch-peptone medium is shown below:

| Composition of the starch-peptone medium | |
|---|---|
| Soluble starch | 1.5% |
| Peptone | 0.5% |
| Yeast extract | 0.5% |
| $KH_2PO_4$ | 0.7% |
| $Na_2HPO_4$ | 0.35% |
| $MgSO_4.7H_2O$ | 0.001% |
| Agar | 2.0% |
| Sodium thioglycolate | 0.1% |
| Tap water | pH 6.4 |

(2) Existence of spore

Formation of spores is observed in agar plate culture using the starch-peptone medium and in submerged culture.

B. Culture Characteristics (1) Shape of colony

Colonies formed in agar plate culture using the starch-peptone medium have the shape of a flat disc of which the center is slightly protuberant, and their peripheral portions are entire. No pigment is formed in the colonies, and the colonies have a luster on the surface and are milk white and opaque. They are cohesive.

(2) Said bacteria are grown by agar plate culture and stab culture both using a putrient broth. The same colonies as in the case of the starch-peptone medium are formed.

| Composition of the nutrient agar | |
|---|---|
| Meat extract | 1.0% |
| Peptone | 1.0% |
| NaCl | 0.2% |
| Sodium thioglycolate | 0.1% |
| Agar | 1.5% |
| Tap water | pH 6.0 |

(3) Stab culture in the nutrient broth

Said bacteria grow with production of a gas containing $H_2$ and $CO_2$. As a result, the rutrient agar is divided in 2 or 3 places.

(4) Submerged culture in nutrient broth

Said bacteria grow only in an anaerobic atmosphere.

| Composition of the nutrient broth | |
|---|---|
| Meat extract | 1.0% |
| Peptone | 1.0% |
| NaCl | 0.2% |
| Sodium thioglycolate | 0.1% |
| Distilled water | pH 6.0 |

(5) Culture in broth-gelatin

Said bacteria do not grow.

| | |
|---|---|
| Meat extract | 1.0% |
| Peptone | 1.0% |
| NaCl | 0.2% |
| Sodium thioglycolate | 0.1% |
| Gelatin | 15% |
| Tap water | pH 6.0 |

(6) Culture in litmus milk

The culture is accompanied by production of a gas, and the medium coagulates hard and is reddended by production of an acid.

C. Physiological Properties (1) Temperature range for growth

Said bacteria grow at 40° C. to 63° C. and do not grow at 30° C. Its growth is satisfactory at about 60° C.

(2) pH range for growth

Said bacteria grow at pH 5 to 7. The growth is satisfactory in the vicinity of pH 5.6.

(3) Behavior toward oxygen

Strictly anaerobic (4) O-F test (Hugh Laifson modified method)

Said bacteria do not grow under an atmosphere of air and is negative. Under anaerobic conditions in a liquid paraffin multilayer, said bacteria grow and produces an acid, so that the culture is yellowed.

| Composition of the medium | |
|---|---|
| Reptone | 0.2% |
| Glucose | 1.0% |
| NaCl | 0.5% |
| $K_2HPO_4$ | 0.03% |
| Sodium thioglycolate | 0.1% |
| Bromcresol purple | 0.002% |
| Agar | 0.3% |
| Tap water | pH 6.0 |

(5) Reduction of nitrate

Negative.

(6) VP test

Negative.

(7) MR test

Positive; the culture is reddened.

(8) Indole production

Measurement is impossible because said bacteria do not grow in aqueous peptone.

(9) Hydrogen sulfide production

Negative in the case of using a Klingrer medium.

(10) Hydrolysis of starch

Positive. Not only soluble starches but also granular starches such as potato starch are hydrolyzed.

(11) Utilization of citric acid

Negative in the case of using a Simmons medium.

(12) Utilization of ammonium salt

Measurement is impossible because said bacteria do not grow in aqueous peptone.

(13) Extracellular production of pigment

Negative.

(14) Oxidase activity

Negative.

(15) Catalase activity
Negative.
(16) Urease activity
Negative.
(17) Utilization of sugars In the following table are shown utilization of sugars and the result of observing whether gas is produced or not by using a Durham fermentation tube.

TABLE 1

| Carbon source | Utilization | Gas production |
|---|---|---|
| Glycerol | − | − |
| D-Xylose | + | + |
| D-Glucose | + | + |
| D-Fructose | + | + |
| D-Mannose | + | + |
| D-Galactose | + | + |
| D-Rhamnose | + | + |
| D-Mannitol | + | + |
| D-Sorbitol | − | − |
| Inositol | − | − |
| Trehalose | + | + |
| Lactose | + | + |
| Maltose | + | + |
| Sucrose | + | + |
| Dextrin | + | + |
| Starch | + | + |
| Inulin | − | − |
| Cellobiose | + | + |

(18) Growth in inorganic salt medium
Said bacteria do not grow.
(19) Production of organic acids
The compositions of organic acids produced from various media are shown in Table 2:

TABLE 2

| Main carbon source of media | Organic acids produced |
|---|---|
| Glucose | Acetic acid |
|  | Lactic acid |
| Dextrin | Acetic acid |
|  | Lactic acid |
| Starch | Lactic acid |
| Mannitol | Lactic acid |
| Sucrose | Acetic acid |
|  | Lactic acid |
| Maltose | Acetic acid |
|  | Lactic acid |
| Rhamnose | Acetic acid |

| Composition of the liquid media tested | |
|---|---|
| Carbon source | 1.0% |
| Peptone | 1.0% |
| Sodium chloride | 0.2% |
| Sodium thioglycolate | 0.1% |
| Distilled water | pH 6.4 |

From these results, said bacteria were identified as bacteria belonging to Clostridium according to the manual of classifying anaerobic bacteria of Holdeman.

Next, enzymatic characteristics of the thermostable α-amylase obtained by using the bacterium of this invention are described below:

The α-amylase activity was assayed in the following manner.

The dextrinizing ability was measured by Blue value method (Chemical Society of Japan, Jikken Kagaku Koza, Vol. 24, Biochemistry II, p279, Maruzen Co., Ltd. (1969)). This method uses the principle that with the progress of hydrolysis of starch molecules, the level of blue color produced due to a starch-iodine complex decreases in proportion to a decrease of the molecular weight. First, 2 ml of a starch solution having a concentration of 2 mg/ml and 1 ml of 0.1M citrate buffer (pH 4.0) were placed in a test tube, and the test tube was shaken in a water bath at 60° C. for 5 minutes. Subsequently, 1 ml of culture filtrate was added as a crude enzyme solution, and the resulting solution was subjected to reaction for 30 minutes. After the reaction is complete, 0.4 ml of the reaction solution was collected and immediately mixed with 2 ml of a 0.5M acetic acid solution to stop the enzyme reaction. Next, 1 ml of the solution thus obtained was added to 10 ml of 1/3000N iodine solution, and the absorbance at 680 nm was measured by means of a spectrophotometer. On the other hand, a part of the reaction solution immediately after the addition of the enzyme solution was collected and subjected to coloration in the same manner as described above, and the absorbance was measured. As the starch, an amylose having a degree of polymerization of about 2,000 was used.

The α-amylase activity was calculated from the following equation:

$$\alpha\text{-Amylase activity (unit)} = \frac{\text{Absorbance of reaction solution at 0 time} - \text{Absorbance of reaction solution at 30 min}}{\text{Absorbance of reaction solution at 0 time}} \times 10.$$

(1) Action and substrate specificity

The enzyme produced by the bacteria of this invention is liquid-type α-amylase which hydrolyzes starches of potato, corn, sweet potato, etc.

(2) Optimum pH

Figure 1:
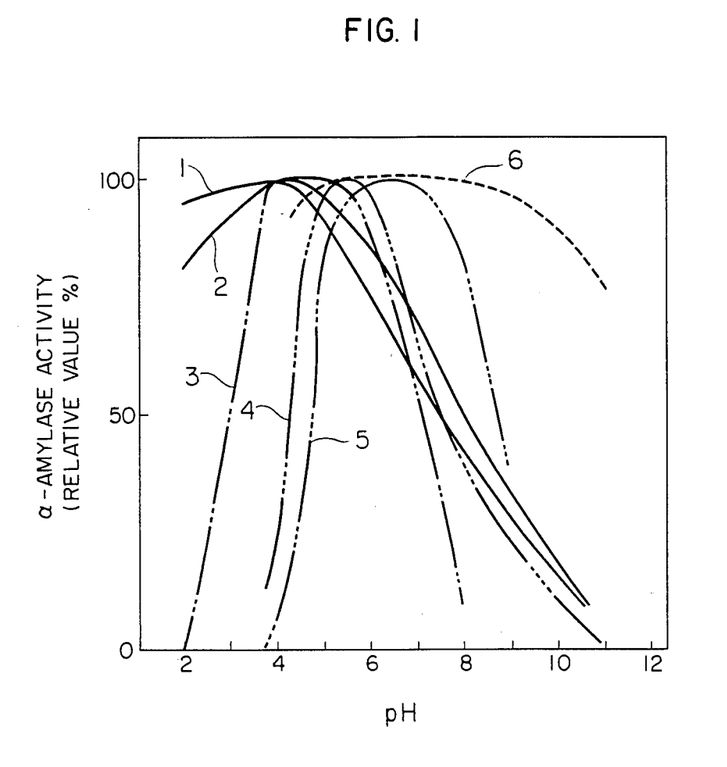
FIG. 1 is a characteristic graph showing the effect of pH on the α-amylase activity (dextrinizing ability) of the thermostable α-amylases produced by the bacterium of this invention and conventional thermostable α-amylases.

Action-pH curves of well-known typical α-amylases are shown in FIG. 1. The α-amylase derived from *Bacillus subtilis* which has been reported by Ogasawara et al. (J. Biochem. 67, 65 (1970)) and is shown by curve 4, the α-amylase of Japanese Patent Application Kokai (Laid-Open) No. 12,946/71 shown by curve 5, and the α-amylase derived from *Bacillus licheniformis* (Japanese Patent Application Kokai (Laid-Open) No. 35,083/73) which has been reported by Saito et al. and is shown by curve 6, have a suitable pH range (a pH range where each α-amylase has 80% of the activity at the optimum pH) at pH 4 to 11. The α-amylase derived from *Bacillus licheniformis* which has reported by Tanaka et al. and has the highest activity on the acidic side among heretofore well-known acid α-amylases (Japanese Patent Application Kokai (Laid-Open) No. 151,970/77, curve 3) has a suitable pH range at pH 3.5 to 6.3 and has no activity at all at pH 2.

On the other hand, α-amylase I (curve 1) and α-amylase II (curve 2) produced by the bacterium of this invention have an optimum pH range at 60° C. at a pH of about 4, have a suitable pH range at pH 2 to 5.7 or pH 2 to 6.3, respectively, and have a high activity even on a more acidic side as compared with the conventional acid α-amylases. That is to say, at pH 2, the conventional acid α-amylases have no activity at all, while the α-amylases produced by the bacterium of this invention have a high activity of 95% or 81%, respectively.

The following reaction system was used for the enzyme reaction:

Enzyme solution: 0.6 to 1.3 μg/ml
Substrate: amylose 1 mg/ml
Citrate buffer: 0.025M.

From the fact that as described above, the α-amylases produced by the bacterium of this invention are different in action pH range from the conventional acid α-amylase, it is evident that they are novel α-amylases.

(3) pH stability

Each of α-amylases I and II produced by the bacterium of this invention was incubated at pH 2, 4, 6 or 7 (0.025M citrate buffer) at 60° C. for 30 minutes. The reaction solution was diluted and then adjusted to pH 4, after which the residual activity was assayed by using amylose as substrate. As a result, both α-amylases entirely retained their activities after the pH treatment described above. Accordingly, the present α-amylases are characterized in that they are stable even in acidic pH ranges.

(4) Optimum temperature

Figure 2:
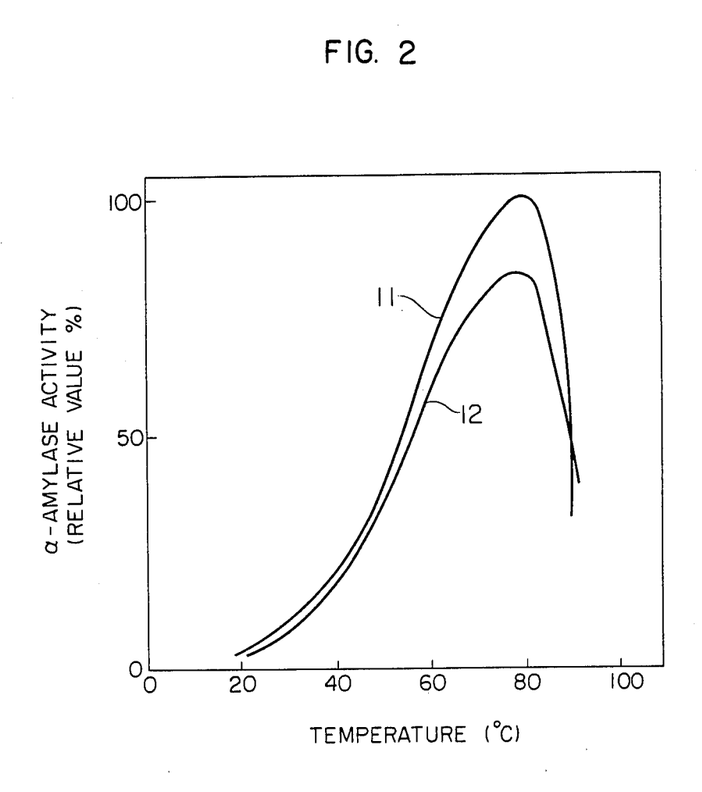
FIG. 2 is a characteristic graph showing the effect of temperature on the α-amylase activity of the thermostable α-amylases produced by the bacterium of this invention.

As shown in FIG. 2, both of the optimum temperatures at the optimum pH of 4.0 of α-amylases I (curve 11) and II (curve 12) produced by the bacterium of this invention are about 80° C. Their suitable temperature (a temperature at which each α-amylase has 80% of the activity at the optimum temperature) is 65° to 87° C. For the reaction, 0.025M citrate buffer was used.

Figure 3:
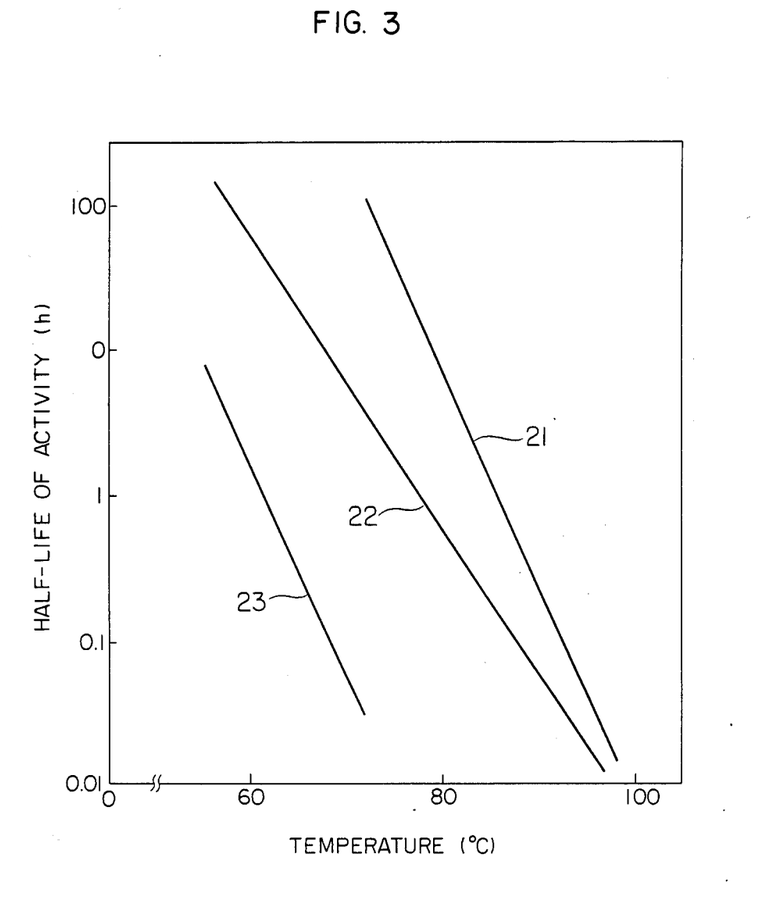
FIG. 3 is a characteristic graph showing the thermostability of the thermostable ≠-amylase produced by the bacterium of this invention and conventional thermostable α-amylases.

(5) Thermostability

α-Amylase II produced by the bacterium of this invention was heated at 60° to 97° C. at pH 6.0 in the presence of 20 μM calcium chloride, and the residual activity was measured. On the basis of the measured values, the half-life of activity at each temperature was determined. The results obtained are shown in FIG. 3. The half-lives of activity (without addition of substrate) at 80° C. and 90° C. are 8 hours and 0.5 hour, respectively. Thus, α-amylase II is excellent in thermostability. α-Amylase I has a half-life of activity at 90° C. of about 0.5 hours, and it is thus equal to α-amylase II in thermostability. On the other hand, as examples of conventional α-amylases, there were used partially pulified α-amylase preparations prepared from culture broths of an α-amylase-producing bacterium belonging to *Bacillus licheniformis* and an α-amylase-producing bacterium belonging to *Bacillus subtilis*, and their half-lives of activity were measured at a calcium concentration of 20 mM. The results obtained are also shown in FIG. 3. The reaction was carried out by use of citrate buffer at pH 6.0 which is the optimum pH of both α-amylases. The half-life of activity at 80° C. of the former α-amylase was 0.6 hour, and the half-life of activity at 70° C. of the latter was 0.6 hour. In thermostability, the α-amylases produced by the bacterium of this invention (curve 21) is inferior to a known thermostable α-amylase of Thermus but is by no means inferior to a thermostable α-amylase of Bacillus (a thermostable α-amylase derived from *Bacillus licheniformis* SP, curve 22).

(6) Effects of metal salts on thermostability

The effects of metal salts on the thermostability of α-amylase II produced by the bacterium of this invention are shown in Table 3. Each of various metal salts was added to an aqueous α-amylase II solution so as to adjust the metal salt concentration to 5 mM, after which the resulting solution was heated and the activity was measured. The percentage of the activity after the heat treatment based on the activity before the heat treatment, namely, the residual activity is shown in terms of %. The heat treatment and the activity measurement are conducted under the following conditions:

Heat Treatment Conditions pH 6.0
Heating temperature: 80° C.
Holding time: 30 minutes

TABLE 3

| Metal salt added (5 mM) | Residual activity (%) |
|---|---|
| Sodium chloride | 79 |
| Potassium chloride | 54 |
| Magnesium chloride | 50 |
| Calcium chloride | 100 |
| Manganese chloride | 15 |
| Nickel chloride | <1 |
| Cobalt chloride | <1 |
| Zinc chloride | <1 |
| No addition | 60 |

The activity measurement was conducted under the following conditions after diluting each sample solution. It was confirmed that addition of each metal salt at said adding concentration had no influence on the activity measurement.

Activity Measurement Conditions pH 4.0 (0.025M citrate buffer)
Activity measurement temperature: 60° C.

As is obvious from Table 1, calcium ion has a protective effect for α-amylase, while ions of sodium, potassium and magnesium have no marked protective effect. On the other hand, ions of nickel, cobalt, zinc and manganese make the thermostability lowered. It was also confirmed that said α-amylase lost its thermostability in the presenct of 0.5 μM EDTA.

Figure 4:
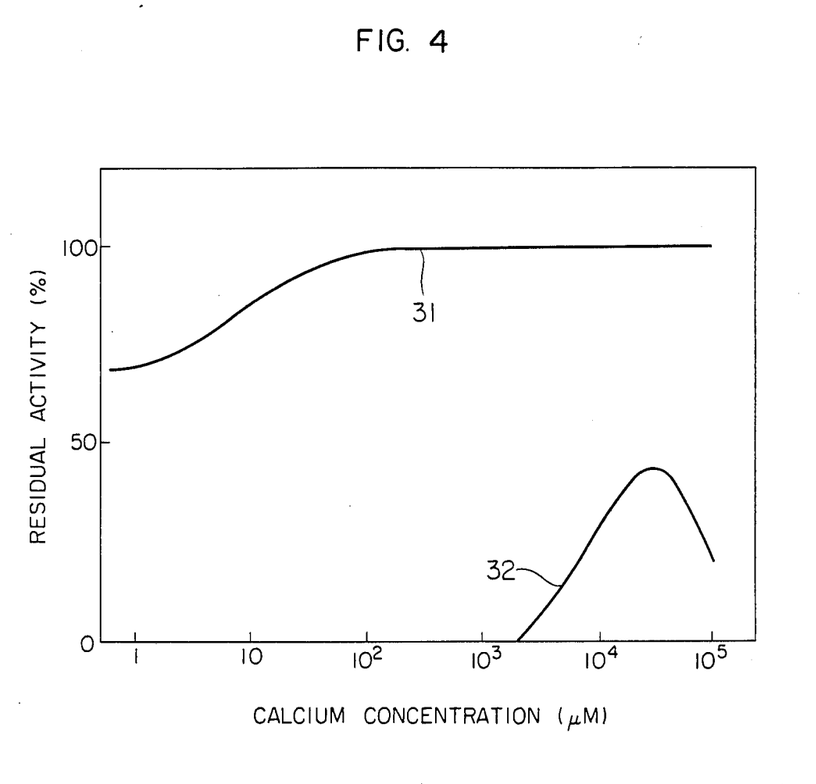
FIG. 4 is a characteristic graph showing the effect of calcium concentration in heat treatment on the α-amylase activity of the thermostable α-amylase produced by the bacterium of this invention and a conventional thermostable α-amylase.

The concentration of calcium required of said α-amylase is 100 μM (4 ppm) as shown in curve 31 in FIG. 4, and said α-amylase is sufficiently stabilized at the calcium concentration in tap water. Further, this enzyme retains 65% of the activity even at a calcium concentration of 1 μM or less. α-Amylase I has a calcium requirement equal to that of α-amylase II.

On the other hand, an α-amylase partially purified from an α-amylase-producing bacterium belonging to *Bacillus licheniformis* requires 30 mM of calcium ion as shown in curve 32 in FIG. 4. The heat treatment was carried out by heating at 80° C. for 30 minutes at pH 6 for both enzymes, and the activity measurement was conducted at 60° C. at respective optimum pH's.

On the other hand, thermostable α-amylase of *Bacillus subtilis* has a concentration of calcium required of 3 to 10 mM (Japanese Patent Application Kokai (Laid-Open) Nos. 44,690/76 and 34,117/83).

Accordingly, the α-amylases of this invention have a much smaller calcium requirement as compared with the known thermostable α-amylases.

(7) Purification method

Since the purification method is described in detail in Examples, it is briefly explained here.

An α-amylase-producing bacterium according to this invention was inoculated into a liquid medium containing starch, peptone and yeast extract, and cultured under anaerobic conditions at 60° C. for 1 to 3 days. Cells and other insoluble substances are removed from the culture broth by centrifugation and the like to obtain a so-called culture filtrate. Subsequently, concentration of α-amylases produced by the bacterium of this invention and removal of impurities are conducted by properly applying well-known methods such as molecular sieve membrane filtration, ion-exchange chromatography, gel filtration chromatography, salting out and the like to the culture filtrate.

(8) Molecular weight

Although the molecular weights of the α-amylases produced according to this invention have not yet been confirmed, they are estimated to be 20,000 or more from their behaviors in molecular sieve membrane filtration.

As described above, the novel thermostable α-amylases produced by the bacterium of this invention are markedly different particularly in action pH and calcium requirement from thermostable enzymes produced by conventional aerobic bacteria.

In producing glucose, isomerized syrup or the like, starch as a starting material is first liquefied by using α-amylase and then saccharified by using clucoamylase. In the liquefaction, the starting starch is charged at as high a concentration as several tens percent, so that the pH of the resulting liquid is acidic. Therefore, in using a conventional α-amylase, a starch fluid is neutralized with an alkali, after which the starch is liquefied. After the liquefaction, the pH of the liquid should be adjusted so as to be acidic again by addition of an acid because well-known glucoamylases are active in an acidic pH range.

When there is used the novel thermostable α-amylase derived from the strictly anaerobic bacterium of this invention, mere employment of water to be charged containing as much calcium as tap water does will do and addition of a calcium agent becomes unnecessary. Moreover, the Ph adjustments in the liquefaction and saccharification steps become unnecessary, so that the burden on a desalting step after the reaction can be greatly reduced.

When the novel thermostable α-amylase produced by culturing the thermophilic anaerobic bacterium belonging to Clostridium of this invention is used for hydrolysis (liquefaction) of starch, water to be charged containing as much calcium as tap water can be used, and conventional addition of calcium becomes unnecessary. Furthermore, the neutralizations in the starch liquefaction and saccharification steps become unnecessary, and as a result, the burden on a desalting step after the reaction can be greatly reduced.

When the novel thermostable α-amylase produced by the process of this invention is used for hydrolysis (liquefaction) of starch, it is sufficient that water to be charged containing as much calcium as tap water does is used, and conventional addition of calcium becomes unnecessary. Moreover, the neutralizations in the starch liquefaction and saccharification steps become unnecessary, so that the burden on a desalting step after the reaction can be greatly reduced.

DETAILED DESCRIPTION OF THE PREFERRED EMBODIMENT

This invention is further explained below in more detail with reference to Examples.

EXAMPLE 1

4.56 Kilograms of liquid media (pH 6.4) containing 1.5% of soluble starch, 0.5% of polypeptone, 0.5% of yeast extract, 0.7% of mono potassium dihydrogen phosphate, 0.35% of disodium hydrogen phosphate, 0.01% of magnesium sulfate heptahydrate, 0.1% of sodium thioglycolate and tap water was divided into three equal parts, and 1.52 g of the media was placed in each of three culture tanks having a capacity of 5 liters and sterilized at 120° C. for 20 minutes. To the media in each tank was added 80 g of a cell suspension of the clostridium separated by the present inventors which had been anaerobically cultured in the same media as described above. Subsequently, a water-sealing trap is attached to the gas outlet, and the gas phase portion in each fermenter was sufficiently replaced with argon gas, after which the bacterium was cultured under anaerobic conditions. The pH of the culture broth was automatically adjusted to 6.0 and its temperature was also automatically adjusted to 60° C. After the bacteria were cultured for 46 hours, the culture broths were combined and centrifuged at 6,000 r.p.m. to remove cells. The supernatant had a specific activity of 49 units/g.

Figure 6:
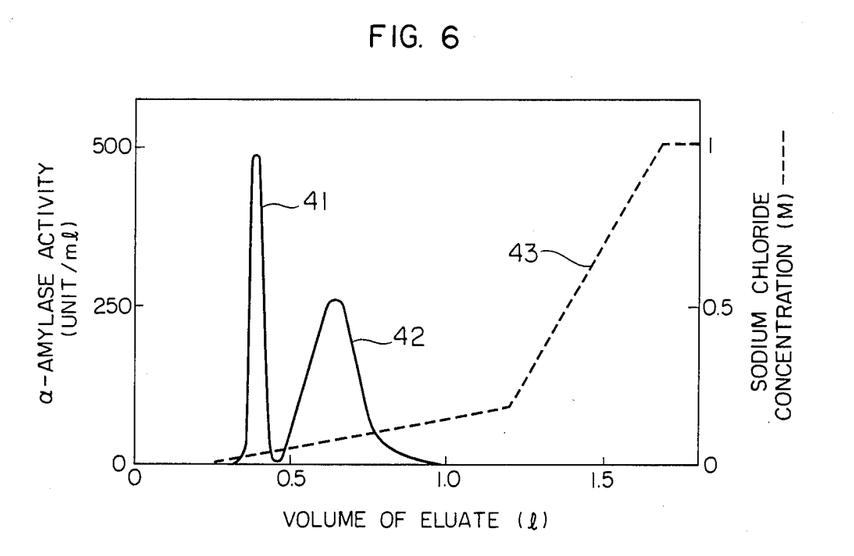
FIG. 6 is an α-amylase activity elution pattern graph of an ion-exchange liquid chromatography using diethylaminoethylated crosslinked dextran gel of the thermostable α-amylases produced by the bacterium of this invention.

Next, 3.5 Kg of the aforesaid supernatant were filtered through a molecular sieve membrane (cut-off molecular weight: 20,000) and the filtrate was concentrated to a volume of 1.5 Kg. The concentrate was divided into two equal parts and 0.75 Kg thereof was charged into a column (diameter: 100 mm, length: 450 mm) packed with crosslinked dextran gel (cut-off molecular weight: 2,500, mfd. by Pharmacia Chemicals) and subjected to molecular sieve liquid chromatography. The elution pattern of α-amylase activity in this case is shown in FIG. 6. The elution was carried out with deionized water and the eluate was fractionated into 100-ml fractions. As shown in FIG. 6, α-amylase activity was observed in the fractions at volumes of eluate of 1.2 to 2 liters. The residual supernatant was also subjected to the same liquid chromatography as described above, and the α-amylase fractions thus obtained were combined with those obtained in the above. The preparation thus obtained was freeze-dried under a vacuum of 40 torr to obtain 2.7 g of dry crude powder.

The specific activity of said crude enzyme dried preparation was 39,000 units/g which was about 800 times the specific activity of the supernatant. The yield of activity was about 60%. In Table 4 are shown the specific activity, yield of activity and recovery of activity of the preparations from the supernatant to the crude enzyme dried preparation.

TABLE 4

| Preparation | Specific activity (unit/g) | Yield (g) | Recovery of activity (%) |
|---|---|---|---|
| Culture filtrate | 49 | 35000 | 100 |
| Concentrate obtained by using a molecular sieve membrane | 92 | 1500 | 81 |
| α-Amylase fraction obtained by molecular sieve liquid chromatography | 73 | 1600 | 66 |
| Crude enzyme dried preparation | 39000 | 2.7 | 60 |

The aforesaid crude enzyme dried preparation was purified by an ion-exchange chromatography (column size: diameter 25 mm, length 400 mm) using diethylaminoethylated crosslinked dextran gel (DEAE-Sephadex, mfd. by Pharmacia Chemicals). In 0.05M Tris-HCl buffer (pH 7.5) was dissolved 2.4 g of the crude enzyme dried preparation. Insoluble substances were removed therefrom by filtration, and the residue was charged into a gel column buffered with the same buffer as described above and was then washed. Subsequently, development was carried out while increasing the sodium chloride concentration in the buffer with a linear gradient (curve 43). The elution pattern of α-amylase activity is shown in FIG. 6. Two peaks having α-amylase activity were observed at elution positions corresponding to sodium chloride concentrations of 0.04M and 0.08M. The former peak is due to α-amylase I (curve 41) and the latter is due to α-amylase II (curve 42). The activity layer of α-amylase I was 30% of the total adsorbed activity, while that of α-amylase II was 60% of the total adsorbed activity. The specific activities of α-amylase I and α-amylase II obtained by freeze-drying each of the two fractions were 390 units/mg and 880 units/mg, respectively, which were 10 times and 23 times, respectively, the specific activity of the crude enzyme dried preparation. The recoveries of the activities based on the centrifugation supernatant of the culture broth were 19% and 35%, respectively.

EXAMPLE 2

In Monod's test tube having a capacity of 40 ml was placed 25 ml of liquid media (pH 6.4) containing 1.5% of glucose, 0.5% of polypeptone, 0.7% of mono potassium dihydrogen phosphate, 0.35% of disodium hydrogen phosphate, 0.01% of magnesium sulfate heptahydrate, 0.1% of sodium thioglycolate and tap water, and iterilized at 120° C. for 20 minutes. To the media was added 1 ml of a culture broth of the clostridium of this invention anaerobically cultured in the same media as described above. Subsequently, a water-sealing trap is attached to the gas outlet, and the gas phase portion in the fermenter was sufficiently replaced with argon, after which the bacteria were cultured under anaerobic conditions at 60° C. for 46 hours. The culture broth thus obtained was centrifuged at 6,000 r.p.m. to remove cells. The supernatant had a specific activity of 10 units/g.

EXAMPLE 3

In Monod's test tube having a capacity of 40 ml was placed 25 ml of a liquid medium (pH 6.4) containing 1.5 g of sucrose, 0.5% of polypeptone, 0.7% of monopotassium dihydrogen phosphate, 0.35% of disodium hydrogen phosphate, 0.01% of magnesium sulfate heptahydrate, 0.1% of sodium thioglycollate and city water, and sterilized at 120° C. for 20 minutes. To the media was added 1 ml of a culture broth of the clostridium of this invention anaerobically cultured in the same media as described above. Subsequently, a water-sealing trap was attached to the gas outlet, and the gas phase portion in the fermenter was sufficiently replaced with argon, after which the bacteria were cultured under anaerobic conditions at 60° C. for 46 hours. The culture broth thus obtained was centrifuged at 6,000 r.p.m. to remove cells. The supernatant had a specific activity of 15 units/g.

EXAMPLE 4

In Monod's test tube having a capacity of 40 ml was placed 25 ml of liquid media (pH 6.3) containing 1.5% of trehalose, 0.5% of polypeptone, 0.7% of monopotassium dihydrogen phosphate, 0.35% of disodium hydrogen phosphate, 0.01% of magnesium sulfate hehtahydrate, 0.1% of sodium thioglycolate and top water, and sterilized at 120° C. for 20 minutes. To the media was added 1 ml of a culture broth of the bacteria belonging to Clostridium of this invention which had been anaerobically cultured in the same media as described above. Subsequently, a water-sealing trap was attached to the gas outlet, and the gas phase portion in the fermenter was sufficiently replaced with argon, after which the bacteria was cultured under anaerobic conditions at 60° C. for 46 hours. The culture broth thus obtained was centrifuged at 6,000 r.p.m. to remove cells. The supernatant had a specific activity of 11 units/g.

EXAMPLE 5

In Monod's test tube having a capacity of 40 ml was placed 25 ml of liquid media (pH 6.2) containing 2.0% of maltose, 0.5% of polypeptone, 0.7% of monopotassium dihydrogen phosphate, 0.35% of disodium hydrogen phosphate, 0.01% of magnesium sulfate heptahydrate, 0.1% of sodium thioglycolate and tap water, and sterilized by heat treatment at 120° C. for 20 minutes. To the media was added 1 ml of a culture broth of the bacteria belonging to Clostridium of this invention which had been anaerobically cultured in the same media as described above. Subsequently, a water-sealing trap was attached to the gas outlet, and the gas phase portion in the fermenter was sufficiently replaced with nitrogen gas of high purity, after which the bacteria were cultured under anaerobic conditions at 60° C. for 46 hours. The culture broth thus obtained was centrifuged at 6,000 r.p.m. to remove cells. The supernatant had a specific activity of 15 units/g.

EXAMPLE 6

In Monod's test tube having a capacity of 40 ml was placed 25 ml of liquid media (pH 6.3) containing 1.5% of D-xylose, 0.7% of monopotassium dihydrogen phosphate, 0.35% of disodium hydrogen phosphate, 0.01% of magnesium sulfate haptahydrate, 0.5% of polypeptone, 0.1% of sodium thioglycolate and top water, and sterilized by heat treatment at 120° C. for 20 minutes. To the media was added 1 ml of a culture broth of the bacteria belonging to Clostridium of this invention which had been anaerobically cultured in the same media as described above. Subsequently, a water-sealing trap was attached to the gas outlet, and the gas phase portion in the fermenter was sufficiently replaced with nitrogen gas of high purity, after which the bacteria were anaerobically cultured at 60° C. for 46 hours. The culture broth thus obtained was centrifuged at 6,000 r.p.m. to remove cells. The supernatant had an α-amylase activity of 12 units/g.

EXAMPLE 7

4.56 Kg of liquid media (pH 6.4) containing 1.5% of soluble starch, 0.5% of polypeptone, 0.5% of yeast extract, 0.7% of monopotassium dihydrogen phosphate, 0.35% of disodium hydrogen phosphate, 0.01% of magnesium sulfate heptahydrate, 0.1% of sodium thioglycolate and tap water was divided into three equal parts, and 1.52 g of the media was placed in each of three culture tanks having a dapacity of 5 liters and sterilized at 120° C. for 20 minutes. To the media in each fermenter was added 80 g of a cell suspension of the clostridium separated by the present inventors which had been anaerobically cultured in the same media as described above. Subsequently, a water-sealing trap was attached to the gas outlet, and the gas phase portion in each fermenter was sufficiently replaced with argon gas, after which the bacteria were cultured under anaerobic conditions. The pH of the culture broth was automatically adjusted to 6.0 and its temperature was also automatically adjusted to 60° C. After the bacteria were cultured for 46 hours, the culture broths were combined and centrifuged at 6,000 r.p.m. to remove cells. The sypernatant had a specific activity of 49 units/g.

Next, 3.5 kg of the aforesaid supernatant was filtered through a molecular sieve membrane (cut-off molecular weight: 20,000) and the filtrate was concentrated to a volume of 1.5 kg. The concentrate was divided into two equal parts and 0.75 kg thereof was charged into a column (diameter: 100 mm, length: 450 mm) packed with crosslinked dextran gel (cut-off of molecular weight: 2,500, mfd. by Pharmacia Chemicals) and subjected to molecular sieve liquid chromatography. The elution pattern of α-amylase activity in this case is shown in FIG. 6. The elution was carried out with deionized water and the eluate was fractionated into 100-ml fractions. As shown in FIG. 6, α-amylase activity was observed in the fractions at volumes of eluate of 1.2 to 2 liters. The residual supernatant was also subjected to the same liquid chromatography as described above, and the α-amylase fractions thus obtained were combined with those obtained in the above. The preparation thus obtained was freeze-dried under a vacuum of 40 torr to obtain 2.7 g of dry crude powder.

The specific activity of said crude enzyme dried preparation was 39,000 units/g which was about 800 times the specific activity of the supernatant. The yield of activity was about 60%. In Table 4 are shown the specific activity, yield of activity and recovery of activity of the preparations from the supernatant to the crude enzyme dried preparation.

TABLE 4

| Preparation | Specific activity (unit/g) | Yield (g) | Recovery of activity (%) |
| --- | --- | --- | --- |
| Culture filtrate | 49 | 35000 | 100 |
| Concentrate obtained by using a molecular sieve membrane | 92 | 1500 | 81 |
| α-Amylase fraction obtained by molecular sieve liquid chromatography | 73 | 1600 | 66 |
| Crude enzyme dried preparation | 39000 | 2.7 | 60 |

EXAMPLE 8

Figure 5:
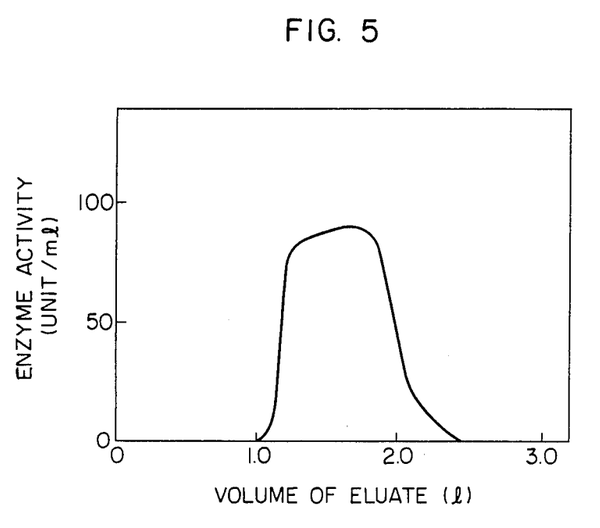
FIG. 5 is an α-amylase activity elution pattern graph of a molecular sieve liquid chromatography using crosslinked dextran gel of the thermostable α-amylase produced by the bacterium of this invention.

The crude enzyme dried preparation prepared in Example 1 was purified by an ion-exchange chromatography (column size: 25φ×400 mm) using diethylaminoethylated crosslinked dextran gel (DEAE-Sephadex, mfd. by Pharmacia Chemicals). In 0.05M Tris-HCl buffer (pH 7.5) was dissolved 2.4 g of the crude enzyme dried preparation. Insoluble substances were removed therefrom by filtration, and the residue was charged into a gel column buffered with the same buffer as described above and was then washed. Subsequently, development was carried out while increasing the sodium chloride concentration in the buffer with a linear gradient (curve 43). The elution pattern of α-amylase activity is shown in FIG. 5. Two peaks having α-amylase activity were observed at elution position corresponding to sodium chloride concentrations of 0.04M and 0.08M. Curve 41 shows α-amylase I and curve 42 α-amylase II. The activity layer of α-amylase I was about 30% of the total adsorbed activity, while that of α-amylase II was 60% by the total adsorbed activity. The specific activities of α-amylase I and α-amylase II obtained by freeze-drying each of the two fractions were 390 units/mg and 880 units/mg, respectively, which were 10 times and 23 times, respectively, the specific activity of the crude enzyme dried preparation. The recoveries of the activities based on the centrifugation supernatant of the culture broth were 19% and 35%, respectively.

We claim:
1. A biologically pure culture of a thermophilic anaerobic bacterium having all of the identifying characteristics of the strain Clostridium sp RS-0001 (FERM P-7918) which produces an α-amylase having the following characteristics:
  (a) half-life of activity in a liquid having 0.02 mM of calcium ionic concentration, pH 6.0, at a temperature of 80° is 8 hours or more;
  (b) activity in a liquid having 0.02 mM of calcium ionic concentration, pH 2.0, at a temperature of 60° C. is 80% or more;
  (c) most optimal pH range wherein the α-amylase has 95% or more of maximum activity, in a liquid having 0.02 mM of calcium ionic concentration at a temperature of 60° C. is 3.4 to 4.5;
  (d) optimal pH wherein the α-amylase has 80% or more of maximum activity in a liquid having 0.02 mM of calcium ionic concentration at a temperature of 60° C. is 2.0 to 6.3; and
  (e) residual activity when heated at 80° C. for 30 minutes in the presence of 1 to 100 μM calcium ionic concentration, without addition of substrate, is 70% or more of the activity when heated at 80° C. for 30 minutes in the presence of more than 100 μM of calcium ionic concentration without addition of substrate.
2. A biologically pure culture of a thermophilic anaerobic bacterium according to claim 1, wherein the bacterium is the strain Clostridium sp RS-0001 (FERM P-7918).

3. A thermostable α-amylase produced by thermophilic anaerobic bacterium belonging to the genus Clostridium which possesses the following characteristics:
   (a) half-life of activity in a liquid having 0.02 mM of calcium ionic concentration, pH 6.0, at a temperature of 80° is 8 hours or more;
   (b) activity in a liquid having 0.02 mM of calcium ionic concentration, pH 2.0, at a temperature of 60° C. is 80% or more;
   (c) most optimal pH range wherein the α-amylase has 95% or more of maximum activity, in a liquid having 0.02 mM of calcium ionic concentration at a temperature of 60° C. is 3.4 to 4.5;
   (d) optimal pH wherein the α-amylase has 80% or more of maximum activity in a liquid having 0.02 mM of calcium ionic concentration at a temperature of 60° C. is 2.0 to 6.3; and
   (e) residual activity when heated at 80° C. for 30 minutes in the presence of 1 to 100 μM calcium ionic concentration, without addition of substrate, is 70% or more of the activity when heated at 80° C. for 30 minutes in the presence of more than 100 μM of calcium ionic concentration without addition of substrate.

4. A thermostable α-amylase according to claim 3, wherein the bacterium is the strain Clostridium sp RS-0001 (FERM P-7918).

5. A process for preparing a thermostable α-amylase which comprises submerged-cultivating anaerobically a thermophilic anaerobic bacterium having all of the identifying characteristics of the strain Clostridium sp RS-0001 (FERM P-7918) which produces an α-amylase having the following characteristics;
   (a) half-life of activity in a liquid having 0.02 mM of calcium ionic concentration, pH 6.0, at a temperature of 80° is 8 hours or more;
   (b) activity in a liquid having 0.02 mM of calcium ionic concentration, pH 2.0, at a temperature of 60° C. is 80% or more;
   (c) most optimal pH range wherein the α-amylase has 95% or more of maximum activity, in a liquid having 0.02 mM of calcium ionic concentration at a temperature of 60° C. is 3.4 to 4.5;
   (d) optimal pH wherein the α-amylase has 80% or more of maximum activity in a liquid having 0.02 mM of calcium ionic concentration at a temperature of 60° C. is 2.0 to 6.3; and
   (e) residual activity when heated at 80° C. for 30 minutes in the presence of 1 to 100 μM calcium ionic concentration, without addition of substrate, is 70% or more of the activity when heated at 80° C. for 30 minutes in the presence of more than 100 μM of calcium ionic concentration without addition of substrate.

6. A process according to claim 5, wherein the bacterium is the strain Clostridium sp RS-0001 (FERM P-7918).

* * * * *